(12) United States Patent
Stolarski et al.

(10) Patent No.: US 11,058,507 B2
(45) Date of Patent: Jul. 13, 2021

(54) SURGICAL DRAPING HOLSTER SYSTEM

(71) Applicants: Edward Stolarski, Sarasota, FL (US); James Scott Hay, Parkland, FL (US)

(72) Inventors: Edward Stolarski, Sarasota, FL (US); James Scott Hay, Parkland, FL (US)

(*) Notice: Subject to any disclaimer, the term of this patent is extended or adjusted under 35 U.S.C. 154(b) by 655 days.

(21) Appl. No.: 15/880,416

(22) Filed: Jan. 25, 2018

(65) Prior Publication Data
US 2018/0206932 A1    Jul. 26, 2018

Related U.S. Application Data

(60) Provisional application No. 62/450,462, filed on Jan. 25, 2017.

(51) Int. Cl.
| | | |
|---|---|---|
| A61B 46/10 | (2016.01) | |
| A61B 50/20 | (2016.01) | |
| A61B 17/00 | (2006.01) | |
| A61B 50/10 | (2016.01) | |

(52) U.S. Cl.
CPC .............. *A61B 46/10* (2016.02); *A61B 50/20* (2016.02); *A61B 17/00234* (2013.01); *A61B 50/10* (2016.02); *A61B 2017/00477* (2013.01)

(58) Field of Classification Search
CPC ... A61B 17/00234; A61B 50/20; A61B 46/10; A61B 50/10; A61B 2017/00477
USPC ..................... 248/689; 206/363; 24/3.1–3.13
See application file for complete search history.

(56) References Cited

U.S. PATENT DOCUMENTS

| | | | | |
|---|---|---|---|---|
| 822,562 | A * | 6/1906 | Tucker | E05C 9/045 292/37 |
| 1,901,613 | A * | 3/1933 | Smith | B62D 43/007 70/259 |
| 2,664,611 | A * | 1/1954 | Shomber | F16B 5/10 24/635 |
| 4,114,933 | A * | 9/1978 | Jankelewitz | E05C 9/06 292/37 |
| 5,112,227 | A * | 5/1992 | Bull | A61B 50/20 206/63.5 |
| 6,260,971 | B1 * | 7/2001 | Cardellini | F16M 11/041 248/177.1 |
| 10,278,790 | B2 * | 5/2019 | Zieris | A61C 19/02 |
| 2016/0075474 | A1 * | 3/2016 | Kinaya | B65D 21/08 206/507 |

* cited by examiner

*Primary Examiner* — Chun Hoi Cheung
(74) *Attorney, Agent, or Firm* — Nicholas R. Lewis, P.A.

(57) ABSTRACT

A storage system, including a storage element having a plurality of receptacles configured to store one or more tools therein, the storage element defining at least one aperture therethrough; an anchoring element configured to at least partially pass through the at least one aperture, the anchoring element having: a substantially cylindrical housing defining a passage therethrough; a plurality of clamping bodies circumscribing the passage and controllably movable towards the passage; and an actuator coupled to housing, where rotational operation of the actuator moves each of the clamping bodies along a substantially linear path towards the passage in order to at least partially obstruct the passage.

14 Claims, 9 Drawing Sheets

SURGICAL DRAPING HOLSTER SYSTEM

CROSS-REFERENCE TO RELATED APPLICATION

This application is related to and claims priority to U.S. Provisional Patent Application Ser. No. 62/450,462, filed Jan. 25, 2017, entitled SURGICAL DRAPING HOLSTER SYSTEM, the entirety of which is incorporated herein by reference.

STATEMENT REGARDING FEDERALLY SPONSORED RESEARCH OR DEVELOPMENT n/a

FIELD OF THE INVENTION

The present disclosure relates to systems for storage configured for use with draping or bedding in a surgical environment, and methods of use thereof.

SUMMARY OF THE INVENTION

The present disclosure advantageously provides a storage system, including a storage element configured to store one or more tools therein, the storage element defining an aperture therethrough; an anchoring element configured to at least partially pass through the aperture, the anchoring element having a housing defining a passage therethrough; a plurality of clamping bodies movably disposed within the housing; and an actuator coupled to the plurality of the clamping bodies, wherein operation of the actuator moves the clamping bodies towards the passage. The system may include an engagement tool configured to pass through the passage of the housing, where the engagement tool includes a first end having at least one of a spiral cut or threaded surface, and a second end opposite the first end that defines a handle. The storage element may include a receptacle sized to accommodate a plurality of medical tools therein in a substantially vertical orientation, and/or the aperture may be substantially perpendicular to a longitudinal axis of the receptacle. The actuator may be rotatably coupled to the housing and/or may define an opening coaxial to the passage of the housing. The actuator may define a substantially spiral groove that matably couples to protrusions on each of the clamping bodies. The plurality of clamping bodies may circumscribe the passage equidistant from each other.

A storage system is disclosed, including a storage element having a plurality of receptacles configured to store one or more tools therein, the storage element defining at least one aperture therethrough; an anchoring element configured to at least partially pass through the at least one aperture, the anchoring element comprising: a substantially cylindrical housing defining a passage therethrough; a plurality of clamping bodies circumscribing the passage and controllably movable towards the passage; and an actuator coupled to housing, wherein rotational operation of the actuator moves each of the clamping bodies along a substantially linear path towards the passage in order to at least partially obstruct the passage. The system may include an engagement tool configured to pass through the passage of the housing, where the engagement tool includes a first end having at least one of a spiral cut or threaded surface, and a second end opposite the first end that defines a handle. The actuator may define an opening coaxial to the passage of the housing, and the opening may be configured to receive at least a portion of the engagement tool therein. Each of the plurality of receptacles may be sized to accommodate a plurality of medical tools therein in a substantially vertical orientation substantially parallel to a longitudinal axis of the receptacles. The at least one aperture may be substantially perpendicular to the longitudinal axis of the receptacles. The actuator may define a substantially spiral groove that matably couples to protrusions on each of the clamping bodies.

A method of anchoring a storage element to a draping is provided, including positioning the storage element adjacent to the draping, wherein the storage element includes a plurality of receptacles configured to store one or more tools therein; coupling an anchoring element to the storage element, wherein the anchoring element defines a passage therethrough, and a plurality of clamping elements controllably movable towards the passage in order to at least partially obstruct the passage; passing an engagement tool through the passage to contact the draping; retracting the engagement tool to pull at least a portion of the draping into the passage; and actuating movement of the clamping elements towards the passage to clamp the draping therein to secure the storage element to the draping. The engagement tool may include a first end having at least one of a spiral cut or threaded surface, and a second end opposite the first end that defines a handle. Actuating movement of the clamping elements may include rotatably manipulating an actuator coupled to a housing of the anchoring element. The actuator may define an opening coaxial to the passage, and the opening may be configured to receive at least a portion of the engagement tool therein. The actuator may define a substantially spiral groove that matably couples to protrusions on each of the clamping bodies. The draping may include surgical draping in a sterile operating environment.

BRIEF DESCRIPTION OF THE DRAWINGS

A more complete understanding of the present disclosure, and the attendant advantages and features thereof, will be more readily understood by reference to the following detailed description when considered in conjunction with the accompanying drawings wherein.

DETAILED DESCRIPTION OF THE INVENTION

The present disclosure provides systems for storage configured for use with draping or bedding in a surgical environment, and methods of use thereof. For example, an example of a storage system 10 is shown in the figures that can be releasably secured to draping, bedding, or other textiles/covering 12 used in an operating or surgical environment to store, hold, and/or otherwise provide easy access to instruments, tools, or other accessories used during the course of a procedure.

Figure 1:
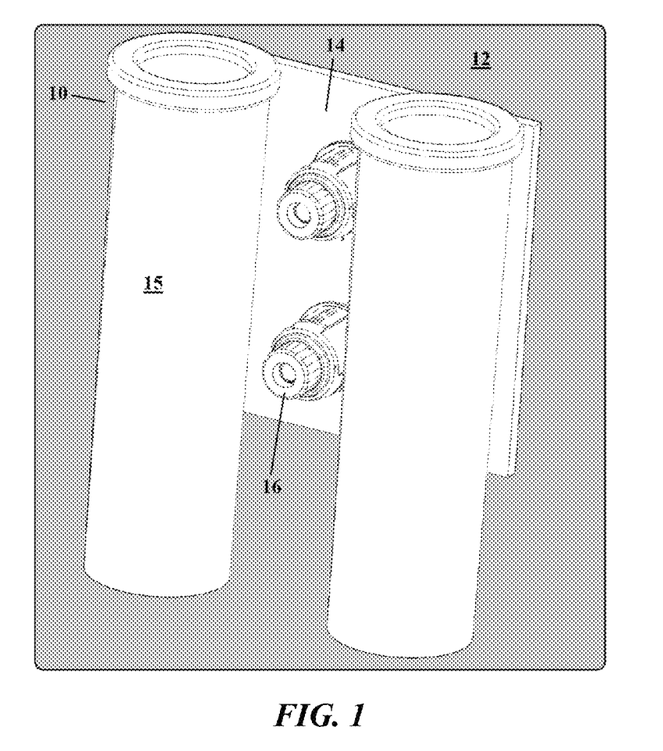
FIG. 1 is a perspective view of an example of a storage system constructed in accordance with the present disclosure.
Figure 2:
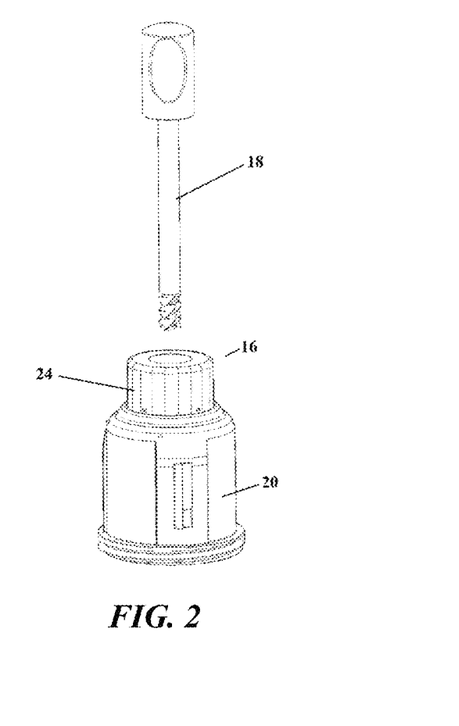
FIG. 2 is an additional view of components of the storage system of FIG. 1.
Figure 3:
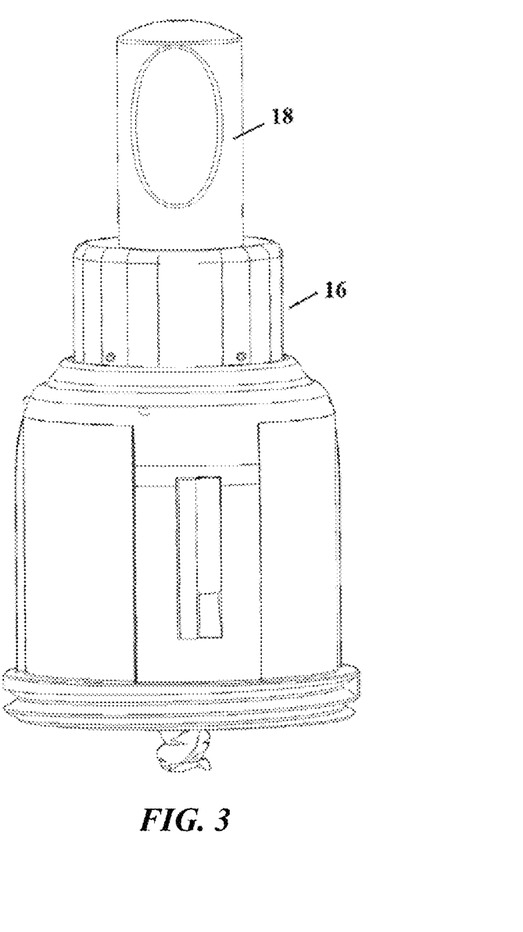
FIG. 3 is another additional view of components of the storage system of FIG. 1.

The system 10 generally includes a storage element 14 that is releasably secured to the draping 12 by one or more fastener or anchoring elements 16. The storage element 14 may provide or define one or more surfaces, receptacles, or container spaces therein or thereon that can accommodate one or more medical instruments, tools, or accessories (not shown) used during a medical procedure. For example, as shown in FIG. 1, the storage element 14 defines two cylindrical, holster-like receptacles 15 to support, retain, or otherwise store instruments or tools. The size, shape, and configuration of the receptacle(s) 15 and/or the storage element 14 may be modified and/or configured to provide desired accessibility, support, and/or storage for tools and/or instruments of varying sizes and shapes, and one or more anchoring elements 16 may be implemented about the storage element 14 to provide secure fixation, as described in more detail herein. The storage element 14 may be constructed from one or more plastics, polymers, metals, and/or composites thereof providing desired strength, weight, and sterilization characteristics for a particular use or application.

Now referring to FIGS. 2-6, an example of the anchoring element 16 is shown with an engagement tool 18 that is usable in conjunction with the anchoring element 16 to releasably secure the anchoring element 16, and thus the storage element 14—to the draping 12. The anchoring element 16 generally defines an outer housing 20, and a passage 22 therethrough that can receive at least a portion of the engagement tool 18 therein. The engagement tool 18 may generally define an elongate body having a handle on a first end thereof to facilitate ease of grasping and manipulation, and a coarse threading, burr, or other tactile feature on an opposite end that can engage or "grab" a portion of the draping 12. In the example shown in the figures, the engagement tool 18 includes threading that can be twisted while in contact with the draping to swirl or otherwise wrap a portion of the draping around the engagement instrument 18.

The anchoring element may include an actuator 24 movably coupled to the housing 20, where the actuator 24 is operable to releasably engage a portion of the draping 12 with the anchoring element 16, as described below. In the example shown in FIGS. 2-6, the actuator 24 is a threaded cap that engages a threaded portion of an inner housing body 26. The inner housing body 26 is coupled to one or more clamping bodies 28 that are movably disposed within the housing 20 about the passage 22 to releasably clamp onto a portion of the draping 12 drawn into the passage 22.

Figure 4:
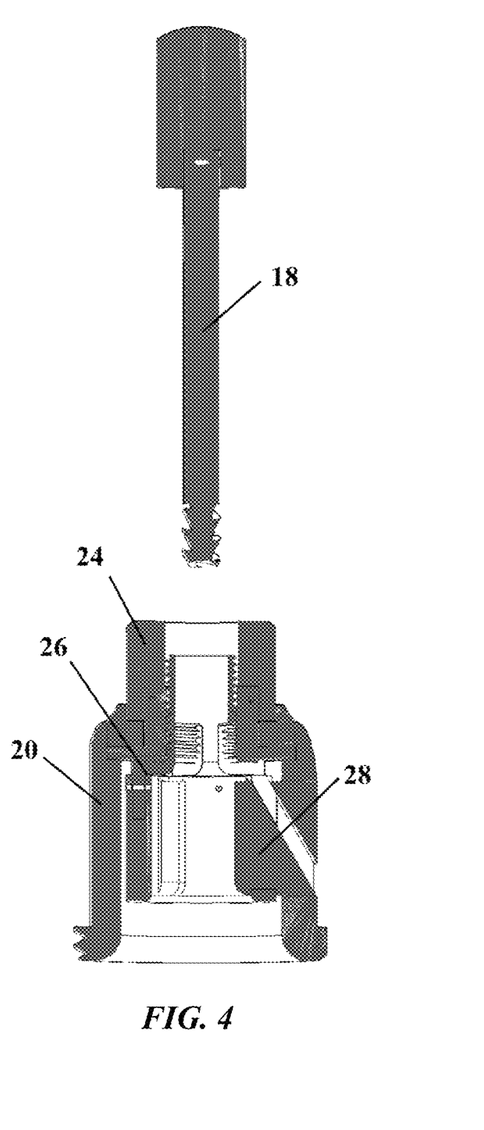
FIG. 4 is a cross-sectional view of components of the storage system of FIG. 1.
Figure 5:
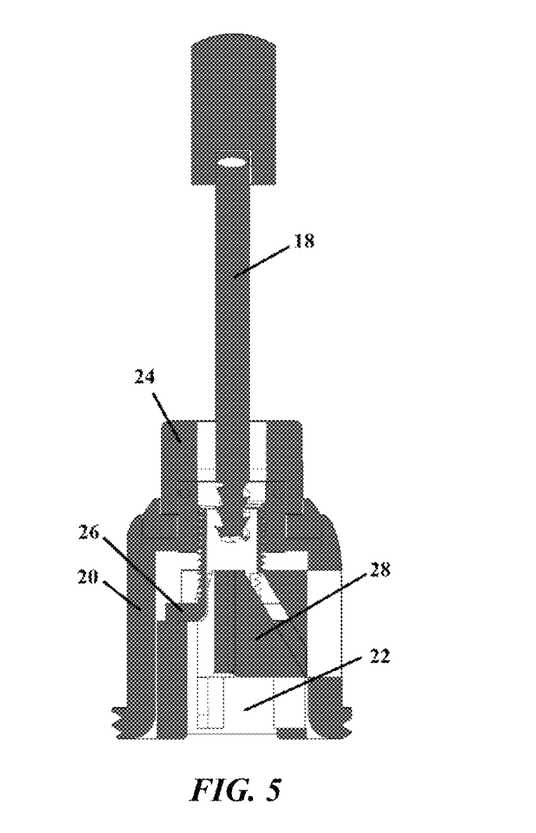
FIG. 5 is an additional cross-sectional view of components of the storage system of FIG. 1.
Figure 6:
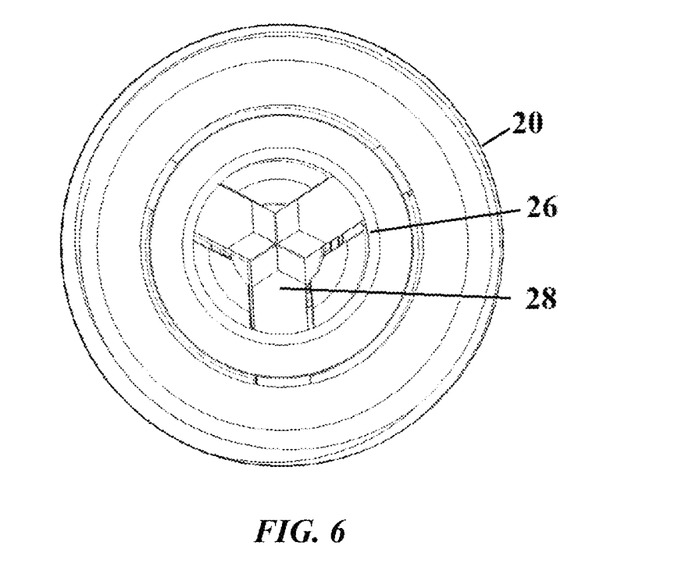
FIG. 6 is a bottom view of components of the storage system of FIG. 1.

In an exemplary operation of the system 10, the anchoring element 16 may be positioned proximate an opening in the storage element 14 and adjacent to a portion of a surgical draping or dressing (such as a portion of the draping or dressing hanging vertically from an operating table or surface). The engagement tool 18 may be passed through the inner passage 22 of the anchoring element 16 and into contact with the draping 12, as show in in FIGS. 2-3 (the draping is excluded from these figures for ease of illustration of the system components). Upon contacting the draping, the engagement tool 18 may be rotated to twistingly engage or otherwise wrap a portion of the draping around the threaded end of the engagement tool 18. The engagement tool 18 may then be pulled outward from the inner passage 22 of the anchoring element 16 as shown in FIG. 4, which consequently pulls the wrapped portion of the draping into the inner passage 22, and proximate to the clamping bodies 28. Once the draping is drawn into the inner passage 22, the actuator 24 may be operated to close the clamping bodies 28 inward towards the draping until sufficient force is exerted by the clamping bodies 28 to secure the anchoring element 16 to the draping. Operation of the actuator 24 may include rotation, which, due to the threaded engagement between the actuator 24 and the inner housing body 26, causes the inner housing body 26 to translate downward. The downward translation of the inner housing body 26, in turn, moves the clamping bodies 28 inward to compress, and thus securely hold, the draping, as shown in FIGS. 5-6. Once the clamping bodies 28 have been moved into a secure position with respect to the draping, the engagement tool 18 can be unwound from the draping, and withdrawn completely from the inner passage 22, thus leaving the anchoring element 16—and the storage element 14—secured to the draping 12.

To disengage the anchoring element 16, the actuator 24 can be turned in an opposite direction, thereby moving the inner housing 26 upward while simultaneously moving the clamping bodies 28 outward to release the draping. The system 10 is then disengaged from the draping, and the system 10 can be sterilized or discarded.

Figure 7:
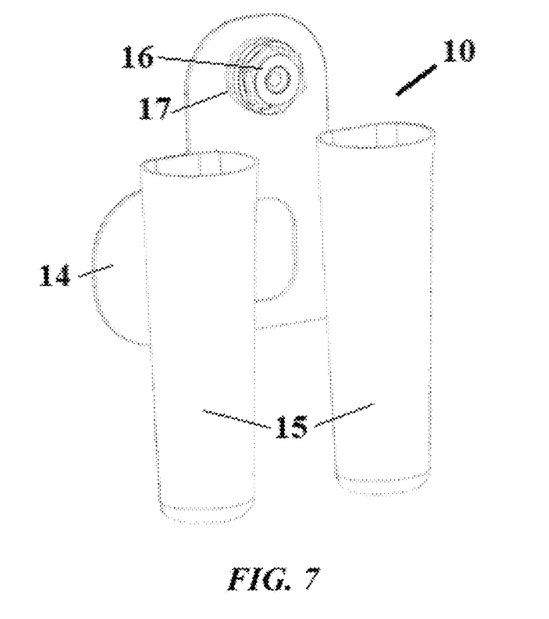
FIG. 7 is a front perspective view of another example of a storage system constructed in accordance with the present disclosure.
Figure 8:
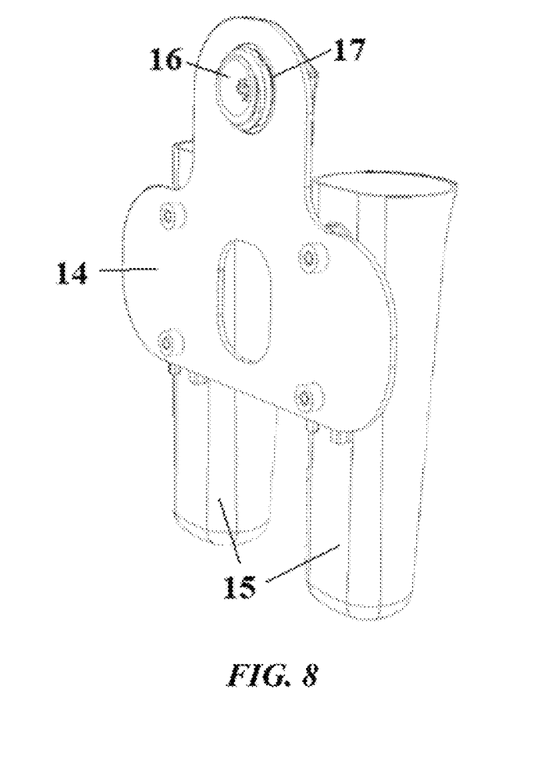
FIG. 8 is a rear perspective view of the storage system of FIG. 7.
Figure 9:
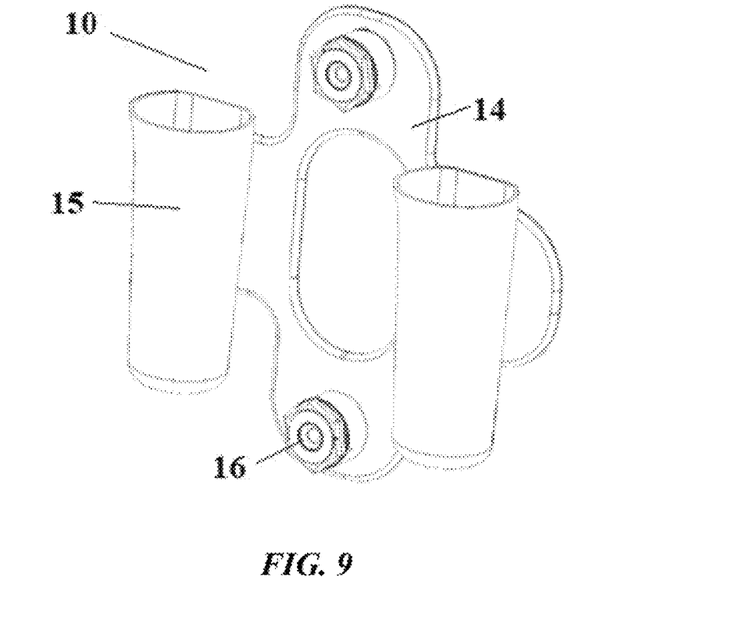
FIG. 9 is a perspective view of another example of a storage system constructed in accordance with the present disclosure.

FIGS. 7-9 illustrate additional examples of the storage element 14 and the receptacles 15 thereof. For example, in FIGS. 7-8, an example is shown where the storage element 14 includes two elongated storage receptacles 15, and is configured to receive a single anchoring element 16 through an aperture 17 in the body or backing of the storage element 14. In the example shown in FIG. 9, the storage element 14 again includes a plurality of storage receptacles 15, but is configured to receive two anchoring elements 16 in respective apertures 17 on the backing or body of the storage element 14. Additional examples of the system 10 disclosed herein may include multiple variations and configurations of storage receptacles 15 and anchoring element 16 to provide the features and operation disclosed herein.

Now referring to FIGS. 10-16, an additional example of an anchoring element 16 and components thereof are illustrated that may be implemented with any of the examples of the storage elements 14 disclosed herein, and is operable substantially similar to the use and methods described above. The anchoring element 16 generally defines a first outer housing 20*a*, a second outer housing 20*b* that couples to the first outer housing 20*a*, and a passage 22 therethrough that can receive at least a portion of the engagement tool 18 therein.

The anchoring element 16 may include an actuator 24 movably coupled to the housing 20, an actuator cap 25 that couples to the actuator 24, and a passage or opening 32 that is coaxial with the passage 22 of the anchoring element 16 to allow passage/receipt of the engagement tool 18 through the actuator 24 during use.

The actuator 24 is rotatably operable to directly drive the clamping bodies 18 to releasably engage a portion of the draping 12 with the anchoring element 16. For example, in this particular example, there are multiple clamping bodies 18 movable disposed within the housing of the anchoring element. The clamping bodies 18 are movable along a linear path towards and away from the passage 22. The movement of the clamping bodies 18 is guided within the housing by one or more inner housing guides 27, which create channels or grooves for the clamping bodies to move along. In the illustrated example, there are three each of the inner housing guides 27 and clamping bodies 18 equidistant from one another and concentrically situated around the passage 22. The inner housing guides are affixed to the housing bodies 20a, 20b by one or more fasteners 30, which may include pins, nails, screws, or the like.

Figure 10:
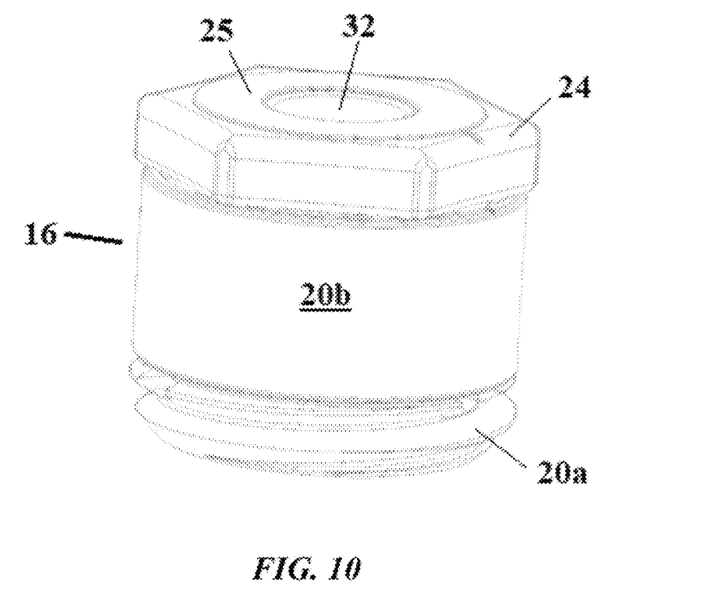
FIG. 10 is a perspective view of an example of an anchoring element constructed in accordance with the present disclosure.
Figure 11:
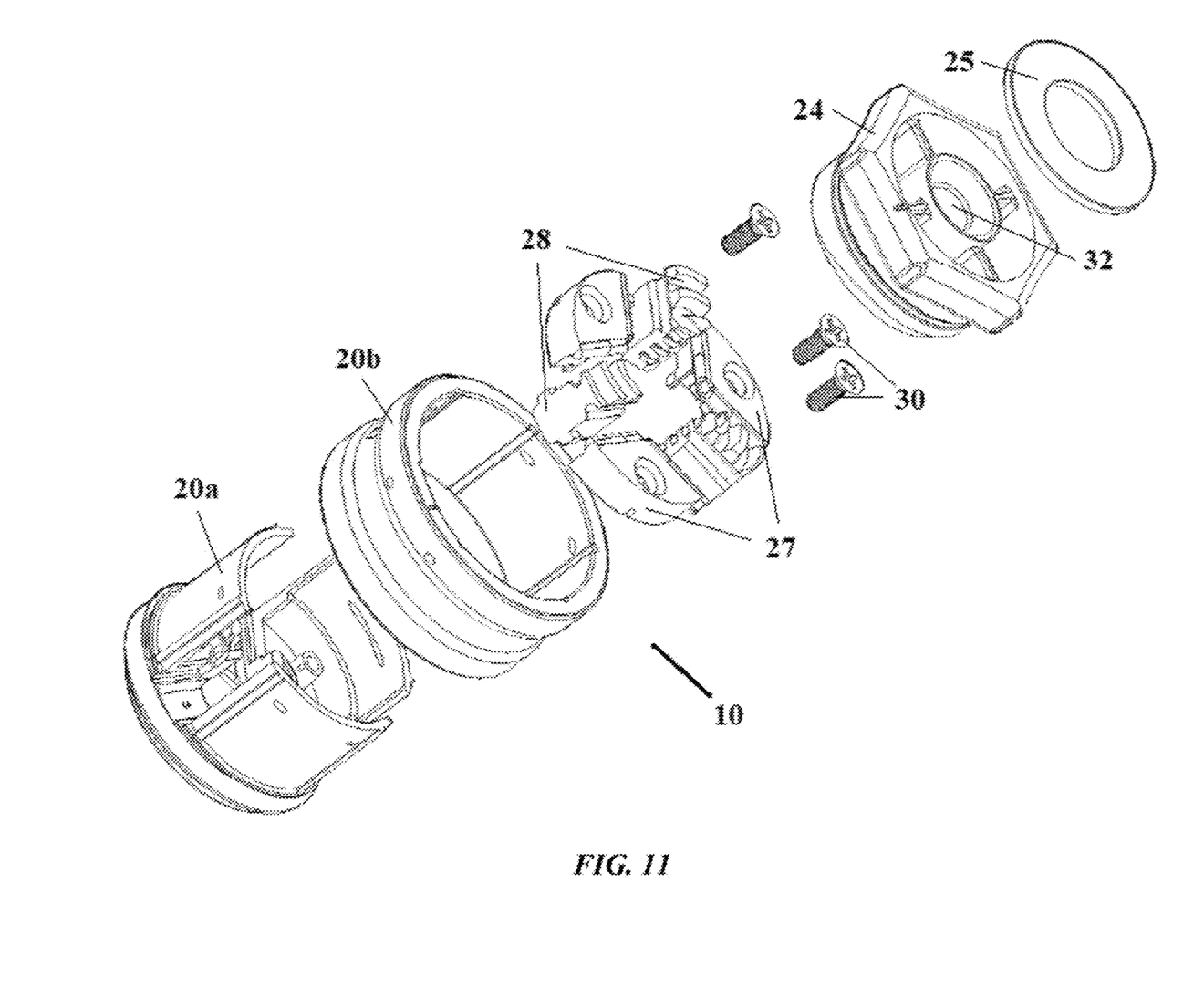
FIG. 11 is an exploded assembly view of the anchoring element of FIG. 10.
Figure 12:
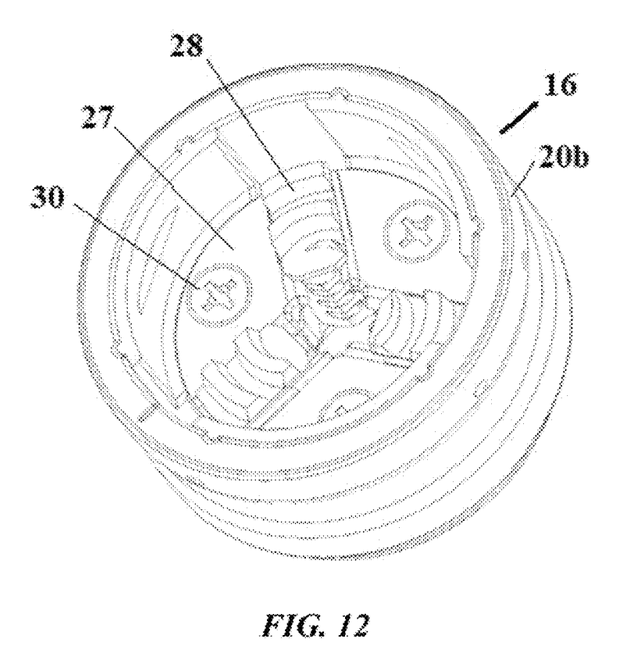
FIG. 12 is another illustration of the anchoring element of FIG. 10.
Figure 13:
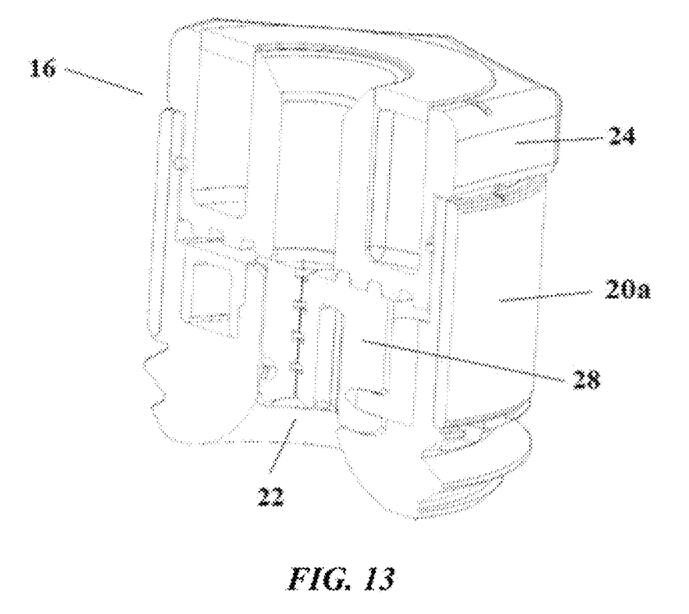
FIG. 13 is a cross-sectional view of the anchoring element of FIG. 10.
Figure 14:
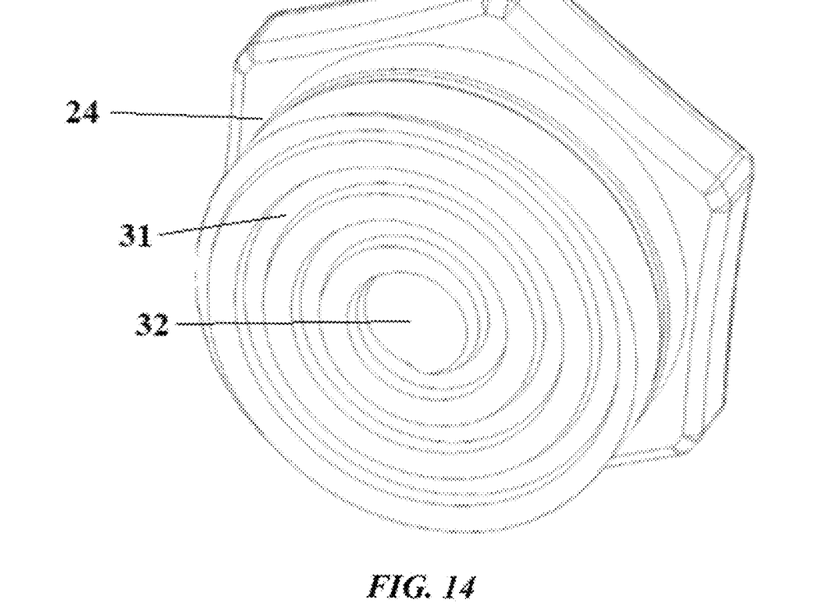
FIG. 14 is an underside view of an example of an actuator for a storage system constructed in accordance with the present disclosure.
Figure 15:
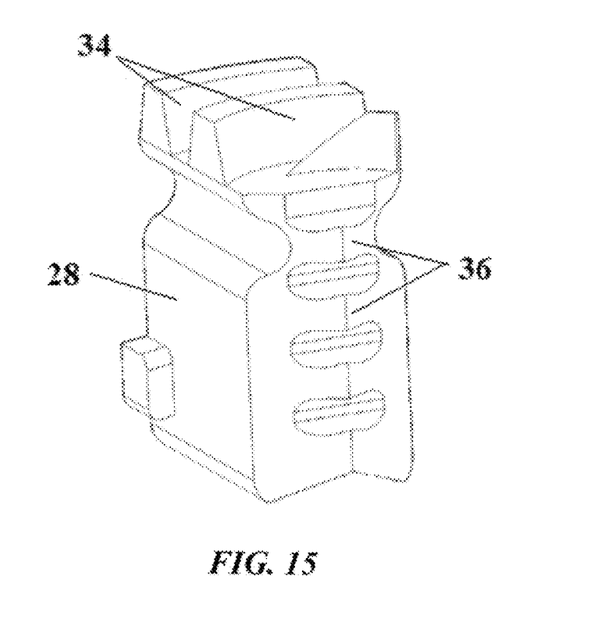
FIG. 15 is a perspective view of an example of a clamping body for a storage system constructed in accordance with the present disclosure.
Figure 16:
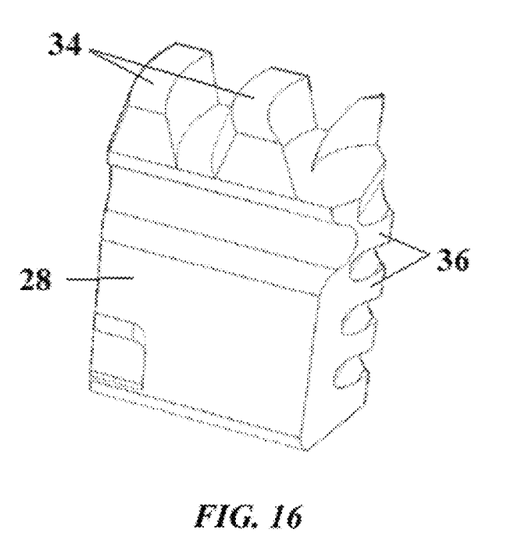
FIG. 16 is another view of the clamping body of FIG. 15.

Continuing to refer to the example of the anchoring element in FIGS. 10-16, the clamping bodies 28 may be directly engaged by the actuator 24. For example, each of the clamping bodies 28 defines a threaded surface and/or curved protrusions 34 on an upper portion thereof, as shown in FIGS. 9-10. These protrusions 34 of the clamping bodies 28 engage the spiral-shaped groove 31 on an underside of the actuator 24, which is shown in FIG. 14. As a result, manipulation of the actuator 24 directly engages and causes inward movement of the clamping bodies 28 to compress, and secure, a portion of the draping within the passage 22. The clamping bodies may further include gripping elements 36 that protrude from a sidewall of the clamping body to pinch or otherwise increase the grip or clamping force that the anchoring element exerts on the draping 12 when in use.

The systems and methods disclosed herein provide a novel anchoring system that can be used without compromising a sterile operating area. In particular, the disclosed system does not pierce the draping material (the inner portion of which typically comes into contact with the patient or at minimum faces the patient and is considered part of the sterile field), but instead clamps onto on the draping. Other fasteners, such as hooks, safety pins, or the like may pierce the draping and potentially compromise the sterile field of operation.

In addition, the anchoring system disclosed herein may be used in other, non-medical applications, including for example, in decorative aspects to hang or anchor decorative items, flower arrangements, or the like. In another example, the anchoring system may be implemented to hang a painter's tools onto a protective canvas or drape in a construction or renovation site.

It will be appreciated by persons skilled in the art that the present disclosure is not limited to what has been particularly shown and described herein above. In addition, unless mention was made above to the contrary, it should be noted that all of the accompanying drawings are not to scale. Of note, the system components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the examples disclosed herein are not necessarily exclusive of each other and may be included in a variety of different combinations or configurations without departing from the scope and spirit of the disclosure. A variety of modifications and variations are possible in light of the above teachings without departing from the scope and spirit of the disclosure, which is limited only by the following claims.

What is claimed is:

1. A storage system, comprising:
    a storage element including a receptacle sized and configured to store one or more tools therein, the storage element defining an aperture therethrough;
    an anchoring element configured to at least partially pass through the aperture, the anchoring element comprising:
        a housing defining a passage therethrough;
        a plurality of clamping bodies movably disposed within the housing; and
        an actuator coupled to the plurality of the clamping bodies, wherein rotational operation of the actuator moves the clamping bodies towards the passage, and wherein the clamping bodies are movable to contact one another within the passage.

2. The system of claim 1, further comprising an engagement tool configured to pass through the passage of the housing, wherein the engagement tool includes a first end having at least one of a spiral cut or threaded surface, and a second end opposite the first end that defines a handle.

3. The system of claim 1, wherein the receptacle is sized to accommodate a plurality of medical tools therein in a vertical orientation.

4. The system of claim 3, wherein a longitudinal axis of the aperture is perpendicular to a longitudinal axis of the receptacle.

5. The system of claim 1, wherein the actuator is rotatably coupled to the housing.

6. The system of claim 5, wherein the actuator defines an opening coaxial to the passage of the housing.

7. The system of claim 6, wherein the actuator defines a spiral groove that matably couples to protrusions on each of the clamping bodies.

8. The system of claim 1, wherein the plurality of clamping bodies circumscribes the passage equidistant from each other.

9. A storage system, comprising:
    a storage element having a plurality of receptacles configured to store one or more tools therein, the storage element defining at least one aperture therethrough;
    an anchoring element configured to at least partially pass through the at least one aperture, the anchoring element comprising:
        a cylindrical housing defining a passage therethrough;
        a plurality of clamping bodies circumscribing the passage and controllably movable towards the passage; and
        an actuator coupled to the housing, wherein rotational operation of the actuator moves each of the clamping bodies along a linear path towards the passage in order to at least partially obstruct the passage.

10. The system of claim 9, further comprising an engagement tool configured to pass through the passage of the housing, wherein the engagement tool includes a first end having at least one of a spiral cut or threaded surface, and a second end opposite the first end that defines a handle.

11. The system of claim 10, wherein the actuator defines an opening coaxial to the passage of the housing, and wherein the opening is configured to receive at least a portion of the engagement tool therein.

12. The system of claim 9, wherein each of the plurality of receptacles are sized to accommodate a plurality of medical tools therein in a vertical orientation parallel to a longitudinal axis of the receptacles.

13. The system of claim 12, wherein a longitudinal axis of the at least one aperture is perpendicular to the longitudinal axis of the receptacles.

14. The system of claim 9, wherein the actuator defines a spiral groove that matably couples to protrusions on each of the clamping bodies.

* * * * *